United States Patent
Hagemeyer et al.

(10) Patent No.: US 9,849,442 B2
(45) Date of Patent: Dec. 26, 2017

(54) METHOD FOR PRODUCING A METAL-CONTAINING SHELL CATALYST WITHOUT INTERMEDIATE CALCINING

(75) Inventors: Alfred Hagemeyer, Bad Aibling (DE); Peter Scheck, Gilching (DE); Gerhard Mestl, Munich (DE); Alice Kyriopoulos, Holzkirchen (DE); Carolin Fischer, Rosenheim (DE)

(73) Assignee: CLARIANT PRODUKTE (DEUTSCHLAND) GMBH, Frankfurt (DE)

( * ) Notice: Subject to any disclaimer, the term of this patent is extended or adjusted under 35 U.S.C. 154(b) by 896 days.

(21) Appl. No.: 13/468,442

(22) Filed: May 10, 2012

(65) Prior Publication Data

US 2012/0289737 A1    Nov. 15, 2012

(30) Foreign Application Priority Data

May 13, 2011 (DE) .................. 10 2011 101 459

(51) Int. Cl.
*B01J 37/02* (2006.01)
*B01J 37/08* (2006.01)
*B01J 37/16* (2006.01)
*B01J 37/18* (2006.01)
*B01J 23/42* (2006.01)
(Continued)

(52) U.S. Cl.
CPC ............... *B01J 23/42* (2013.01); *B01J 23/44* (2013.01); *B01J 23/50* (2013.01); *B01J 23/52* (2013.01); *B01J 23/58* (2013.01); *B01J 23/66* (2013.01); *B01J 35/008* (2013.01); *B01J 37/0221* (2013.01); *B01J 37/08* (2013.01); *B01J 37/16* (2013.01); *C07C 67/055* (2013.01);
(Continued)

(58) Field of Classification Search
CPC ... B01J 23/42; B01J 23/44; B01J 23/50; B01J 23/52; B01J 23/66; B01J 37/0215; B01J 37/0234; B01J 37/08; B01J 37/16; B01J 37/18; B01J 35/008
USPC ....... 502/330, 333, 334, 339, 344, 347, 348, 502/355, 439
See application file for complete search history.

(56) References Cited

U.S. PATENT DOCUMENTS 5,066,365 A     11/1991   Roscher et al.
5,122,496 A *    6/1992   Vorlop et al. ............... 502/245
(Continued)

FOREIGN PATENT DOCUMENTS

CN    101730584 A    6/2010
DE    197 34 974 A1   2/1999
(Continued)

OTHER PUBLICATIONS

German office Action issued on Nov. 14, 2011, in related German Application No. 10 2011 101 459.8, including English translation.

*Primary Examiner* — Cam N. Nguyen
(74) *Attorney, Agent, or Firm* — Anthony Bisulca (57) ABSTRACT

A method for producing a shell catalyst which comprises, in the outer shell, one or more of the following metals: Pd, Pt, Ag and Au. Also the use of the shell catalyst produced using the method according to the invention for the production of vinyl acetate monomer, in the hydrogenation of hydrocarbons, in particular the selective hydrogenation of polyunsaturated hydrocarbon compounds, or in the oxidation of alcohols to ketones/aldehydes/carboxylic acids.

20 Claims, 1 Drawing Sheet (51) Int. Cl.
  *B01J 23/44*    (2006.01)
  *B01J 23/50*    (2006.01)
  *B01J 23/66*    (2006.01)
  *B01J 35/00*    (2006.01)
  *B01J 23/52*    (2006.01)
  *B01J 23/58*    (2006.01)
  *C07C 67/055*   (2006.01)
  *B01J 21/04*    (2006.01)
  *B01J 21/08*    (2006.01)

(52) U.S. Cl.
  CPC ............... *B01J 21/04* (2013.01); *B01J 21/08* (2013.01); *Y02P 20/582* (2015.11)

(56) References Cited

U.S. PATENT DOCUMENTS

| | | | |
|---|---|---|---|
| 5,498,590 A * | 3/1996 | Burmeister et al. | 502/439 |
| 5,854,171 A * | 12/1998 | Nicolau et al. | 502/330 |
| 6,015,769 A | 1/2000 | Wang | |
| 6,268,522 B1 * | 7/2001 | Hagemeyer et al. | 560/245 |
| 6,579,824 B1 * | 6/2003 | Herzog et al. | 502/302 |
| 6,603,038 B1 | 8/2003 | Hagemeyer et al. | |
| 7,534,737 B2 * | 5/2009 | Gajda | 502/60 |
| 7,744,675 B2 * | 6/2010 | Saukaitis et al. | 95/55 |
| 8,216,964 B2 | 7/2012 | Wang et al. | |
| 8,466,082 B2 * | 6/2013 | Hagemeyer et al. | 502/339 |
| 8,586,780 B2 * | 11/2013 | Hagemeyer et al. | 560/247 |
| 2002/0087042 A1 * | 7/2002 | Schmidt et al. | 585/654 |
| 2003/0036476 A1 * | 2/2003 | Arnold et al. | 502/325 |
| 2003/0187294 A1 * | 10/2003 | Hagemeyer et al. | 560/241 |
| 2005/0203320 A1 * | 9/2005 | Ryu | 585/261 |
| 2010/0190638 A1 | 7/2010 | Hagemeyer et al. | |
| 2010/0197488 A1 * | 8/2010 | Hagemeyer et al. | 502/242 |
| 2010/0197956 A1 | 8/2010 | Hagemeyer et al. | |
| 2010/0261603 A1 * | 10/2010 | Hagemeyer et al. | 502/339 |

FOREIGN PATENT DOCUMENTS

| | | |
|---|---|---|
| DE | 197 34 975 A1 | 3/1999 |
| DE | 10 2007 025 356 A1 | 1/2009 |
| JP | 2007-514542 | 6/2007 |
| WO | WO 99/62632 | 12/1999 |
| WO | WO 2005/065820 | 7/2005 |

* cited by examiner

METHOD FOR PRODUCING A METAL-CONTAINING SHELL CATALYST WITHOUT INTERMEDIATE CALCINING

CROSS REFERENCE TO RELATED APPLICATIONS

This is a U.S. application claiming priority benefit of German Patent Application Number 10 2011 101 459.8 (filed May 13, 2011), the content of such application being incorporated herein by reference.

BACKGROUND

Supported catalysts containing one or more metals from the group consisting of palladium, platinum, silver and gold have already been known for some time. Catalysts containing palladium or platinum and gold are preferably used in the synthesis of vinyl acetate from a reaction mixture of ethylene, oxygen and acetic acid. Various production methods for such supported catalysts are already known. Supported catalysts containing palladium and platinum, palladium or platinum and silver or gold, or palladium, silver and gold are likewise used in the hydrogenation of hydrocarbons, in particular the selective hydrogenation of polyunsaturated hydrocarbon compounds. Catalysts containing silver and/or gold are preferably used in the oxidation of alcohols to ketones/aldehydes/carboxylic acids. Thus, for example, precursor compounds which contain the corresponding metals are applied, dissolved preferably in an aqueous solution, to the surface of a support body. The support body containing the corresponding precursor compounds is then usually calcined under oxidic conditions in a high-temperature oven, wherein the metal-containing precursor compounds are converted into the metal oxides. The support bodies which contain the corresponding metal oxides are then subjected to reduction to the elemental metals in a separate unit. The fact that this method is carried out in two stages in separate units makes it laborious and cost-intensive. In addition, the starting materials are usually chloride-containing precursor compounds, which as a rule are very stable and therefore require high temperatures for decomposition to the metal oxides before they can be converted into the elemental metals by reduction.

It was therefore desirable to provide a method that is more cost-effective and more energy-saving than previously known methods, without the occurrence of significant losses of selectivity and activity during the reaction catalyzed by the catalyst.

SUMMARY

An aspect of the present invention relates to a method for producing a shell catalyst which comprises, in the outer shell, one or more of the following metals: Pd, Pt, Ag and Au. Another aspect of the present invention relates to the use of the shell catalyst produced using the method according to the invention for the production of vinyl acetate monomer, in the hydrogenation of hydrocarbons, in particular the selective hydrogenation of polyunsaturated hydrocarbon compounds (in particular acetylene), or in the oxidation of alcohols to ketones/aldehydes/carboxylic acids.

It was surprisingly found that, starting from substantially chloride-free metal-containing precursor compounds, a precalcining before the reduction to the metals can be dispensed with and the reduction of the metal components of the metal-containing precursor compounds can be carried out either directly in an inert gas atmosphere or a reducing atmosphere, or by first decomposing the precursor compounds under inert gas and optionally then reducing the metal components of the precursor compounds to the elemental metals by switching from inert gas to a reducing atmosphere. This method has the advantage that there is no need for an explicit precalcining to the metal oxides from the metallic precursor compounds in for example a separate belt calcining apparatus before the reduction to the elemental metals is carried out in a further unit. Time- and cost-intensive heating and cooling rates can consequently be dispensed with by transferring the precalcined support body from a calcining device, e.g. belt calcining apparatus, into a device in which the metal components of the precursor compounds are reduced into the elemental metals. Furthermore, by dispensing with the intermediate calcining, the mechanical stress and thus wear/fracture during the loading/emptying of the calcining oven is greatly reduced. In addition, the use of substantially chloride-free precursor compounds makes it possible to carry out the decomposition or reduction of the metal components of the precursor compounds at relatively low temperatures, which further make the method cost-effective and energy-saving. By "chloride-free" is meant that chlorine is neither bound in the form of a chlorine ligand nor present as chloride ions in a (complex) salt. By "substantially" is meant that it cannot be ruled out that, because of their production or the choice of the educt, corresponding chlorine- or chloride-free compounds contain unavoidable small levels of contamination of chlorine- or chloride-containing compounds.

DETAILED DESCRIPTION

An aspect of the present invention provides for a method for producing a shell catalyst, in which a substantially chloride-free Pd-, Pt-, Ag- or Au-containing precursor compound is applied to a support body and the support body with the applied precursor compound is subjected to a temperature treatment in the range of from 80° C. to 500° C. in a non-oxidizing atmosphere.

The choice of Pd-, Pt-, Ag- or Au-containing precursor compounds is decisive for the method according to an aspect of the invention. The step of intermediate calcining to the metal oxides between the steps of applying the precursor compound to the support body and the reduction can thereby be dispensed with. It was established that this method is not readily transferable to the production of other catalysts with other metals, as here the precalcining to metal oxides usually represents an essential step for the quantitative reduction to the elemental metals. This is true in particular for the choice of Ag- or Au-containing precursor compounds.

By the term "shell catalyst" is meant a catalyst which comprises a support body and a shell with catalytically active material, wherein the shell can be formed in two different ways:

Firstly, a catalytically active material can be present in the outer area of the support body, with the result that the material of the support body serves as matrix for the catalytically active material and the area of the support body which is impregnated with the catalytically active material forms a shell around the unimpregnated core of the support body. Secondly, a layer in which a catalytically active material is present can be applied to the surface of the support body. This layer forms the shell of the support body. In the latter variant, the support body material is not a constituent of the shell, but the shell is formed by the catalytically active material itself or a matrix material which comprises a catalytically active material. In an embodiment of the present invention, this is preferably the first-named variant of a shell catalyst.

In the catalysts produced using the method according to an aspect of the invention, the metals are present either in monoatomic form or in the form of aggregates. However, they are preferably present in the form of aggregates. These monoatomic atoms or aggregates are dispersed predominantly uniformly inside the shell of the shell catalyst.

The shell thickness of the outer shell of the support body is preferably 1 to 70%, more preferably 2 to 60%, even more preferably 3 to 50% and most preferably 4 to 40% of half of the total thickness of the support body. The named percentage therefore relates to half of the total thickness as, depending on the shape of the support body during production, e.g. by spray impregnation with a solution containing precursor compound, the precursor compound either penetrates the support body material from two outer surfaces (sphere) or, if the support body material has a more complex shape, such as e.g. that of a hollow cylinder, there are an outer surface and an inner surface which the precursor compound penetrates. The outer shell boundary is equalized with the outer boundary of the metal-containing support body. By inner shell boundary is meant the boundary, located inside the support body, of the outer metal-containing shell which is at such a distance from the outer shell boundary that 95 wt.-% of all of the metal contained in the support body is located in the outer shell. However, the shell thickness is preferably not more than 70%, by preference not more than 60%, more preferably not more than 50%, even more preferably not more than 40% and most preferably not more than 30%, in each case relative to half of the total thickness of the support body.

The metal-impregnated support body preferably contains no more than 5% of the total metal in its inner area, thus the area inside the outer shell.

With regard to the shell thickness of the catalyst, the maximum concentration of metal preferably lies in the area of the outer shell, particularly preferably at the outer edge of the outer shell. The metal concentration preferably decreases towards the inner shell boundary.

The support body preferably consists of an inert material. It can be porous or non-porous. However, the support body is preferably porous. The support body preferably consists of particles with a regular or irregular shape, such as for example spheres, tablets, cylinders, solid cylinders or hollow cylinders, rings, stars or other shapes, and its dimensions, such as e.g. diameter, length or width, are in a range of from 1 to 10 mm, preferably 3 to 9 mm. Spherical, i.e. e.g. sphere-shaped, particles with a diameter of from 3 to 8 mm are preferred according to aspects of the invention. The support body material can be composed of any non-porous and porous substance, preferably porous substance. Examples of materials for this are titanium oxide, silicon oxide, aluminium oxide, zirconium oxide, magnesium oxide, silicon carbide, magnesium silicate, zinc oxide, zeolites, sheet silicates and nanomaterials, such as for example carbon nanotubes or carbon nanofibres, preferably when the support body material itself is a heterogeneous catalyst.

The above-named oxidic support body materials can be used for example in the form of mixed oxides or defined compositions, such as for example $TiO_2$, $SiO_2$, $Al_2O_3$, $ZrO_2$, MgO, SiC or ZnO. Furthermore, soots, ethylene black, charcoal, graphite, hydrotalcites or further support body materials known per se to a person skilled in the art can preferably be used in different possible modifications. The support body materials can preferably be doped for instance with alkali or alkaline earth metals or also with phosphorus, halide and/or sulphate salts.

The BET surface area of the support body material without the coating with the precursor compounds is 1 to 1,000 $m^2/g$, preferably 1 to 600 $m^2/g$, particularly preferably 1 to 400 $m^2/g$. The BET surface area is determined using the 1-point method by absorption of nitrogen in accordance with DIN 66 132.

In addition, it can be preferred that the integral pore volume of the support body material (determined in accordance with DIN 66 133 (Hg porosimetry)) without the coating with the precursor compound is greater than 0.1 ml/g, preferably greater than 0.18 ml/g.

The support body is usually produced by subjecting a plurality of support bodies to a "batch" process, in the individual process steps of which the shaped bodies are subject to relatively high mechanical stress for example by using stirring and mixing tools. In addition, the shell catalyst produced by the method according to the invention can be subjected to a strong mechanical load stress during the filling of a reactor, which can result in an undesired formation of dust as well as damage to the support body, in particular to its catalytically active shell located in an outer area.

In particular, to keep the wear of the catalyst produced by the method according to the invention within reasonable limits, the shell catalyst has a hardness greater than/equal to 20 N, preferably greater than/equal to 25 N, further preferably greater than/equal to 35 N and most preferably greater than/equal to 40 N. The hardness is ascertained by means of an 8M tablet-hardness testing machine from Dr. Schleuniger Pharmatron AG, determining the average for 99 shell catalysts, after drying of the catalyst at 130° C. for two hours, wherein the apparatus settings are as follows:

Distance from the shaped body: 5.00 mm
Time delay: 0.80 s
Feed type: 6 D
Speed: 0.60 mm per second The hardness of the catalyst produced by the method according to aspects of the invention can be influenced for example by means of variations in certain parameters of the method for producing the support body, for example by the calcining time and/or the calcining temperature for the support body. The just-mentioned calcining is not a calcining of the support body impregnated with the metal-containing precursor compounds, but merely a calcining step for producing the support body before the precursor compounds are applied.

It is also preferred that 80% of the integral pore volume of the support body is formed by mesopores and macropores, preferably at least 85% and most preferably at least 90%. This counteracts a reduced activity, effected by diffusion limitation, of the catalyst produced by the method according to aspects of the invention, in particular in the case of metal-containing shells with relatively large thicknesses. By the terms micropores, mesopores and macropores are meant in this case pores which have a diameter of less than 2 nm, a diameter of from 2 to 50 nm and a diameter of more than 50 nm respectively.

The smaller the thickness of the outer shell of the catalyst is, the higher the activity of the shell catalysts produced by the method according to the invention generally is. According to a further preferred embodiment of the catalyst produced by the method according to aspects of the invention, the shell of the catalyst therefore has a thickness in the range of from 5 μm to 2000 μm, preferably from 10 μm to 1500

μm, more preferably from 15 to 1000 μm. If the shell catalyst is to be used for example as catalyst for the synthesis of vinyl acetate, its shell thickness preferably lies in the range of from 100 μm to 400 μm, more preferably in the range of from 150 μm to 300 μm. If the shell catalyst is to be used as hydrogenation catalyst, for example for the selective hydrogenation of acetylene, its shell thickness preferably lies in the range of from 10 μm to 200 μm, more preferably in the range of from 20 μm to 150 μm and most preferably in the range of from 30 μm to 100 μm. If the shell catalyst is to be used for example as catalyst for the oxidation of alcoholic hydrocarbon compounds to aldehydes, ketones or carboxylic acids, its shell thickness preferably lies in the range of from 100 μm to 2000 μm, more preferably in the range of from 200 μm to 1000 μm.

The thickness of the shell can be measured visually by means of a microscope. The area in which the metal is deposited appears black, while the areas free of noble metals appear white. As a rule, the boundary between areas containing noble metals and areas free of them is very sharp and can be clearly recognized visually. If the above-named boundary is not sharply defined and accordingly not clearly recognizable visually, the thickness of the shell corresponds—as already mentioned—to the thickness of a shell, measured starting from the outer surface of the catalyst support, which contains 95% of the noble metal deposited on the support.

In order to ensure a largely uniform activity of the catalyst produced by the method according to aspects of the invention over the thickness of the noble metal-containing shell, the noble-metal concentration should vary only relatively little over the shell thickness. It is therefore preferred if, over an area of 90% of the shell thickness, wherein the area is at a distance of 5% of the shell thickness from each of the outer and inner shell limits, the profile of the noble-metal concentration of the catalyst varies from the average noble-metal concentration of this area by a maximum of +/−20%, preferably by a maximum of +/−15% and by preference by a maximum of +/−10%. Such profiles can be obtained by means of the spraying-on described further below in a fluidized bed, a fluid bed or an Innojet AirCoater.

In the method according to aspects of the invention, it is preferred if, before or after the temperature treatment, a further substantially chloride-free Pd-, Pt-, Ag- or Au-containing precursor compound is applied to the support body. In other words, two precursor compounds are applied to the support body either sequentially or simultaneously. It may be that the two precursor compounds are applied to the support body from one solution and the temperature treatment is then carried out. In this case, the precursor compounds are preferably different in terms of the choice of the metals. However, it may also be that the two precursor compounds are applied to the support body successively from different solutions. It may be that the temperature treatment lies between these two application steps, but it may also be that the temperature treatment is carried out only when both precursor compounds have been applied. In these cases, the precursor compounds can be the same as or different to, preferably different to, each other. However, it is particularly preferred that the two metals are applied before the temperature treatment from one solution.

It is, however, also in accordance with aspects of the invention that three different precursor compounds are applied to the support body either sequentially from different solutions or simultaneously from the same solution, and the (first) temperature treatment is then carried out. In this case, to produce a hydrogenation catalyst for the selective hydrogenation of acetylene, Pd-, Ag- and Au-containing precursor compounds are preferably applied simultaneously, and only then is the temperature treatment carried out.

If no further (second or third) precursor compound is applied to the support body, the one applied precursor compound is preferably an Ag- or Au-containing precursor compound, preferably an Ag-containing precursor compound.

The following different pairs of precursor compounds can be applied to the support body either simultaneously or successively, preferably in the form of a solution:
 (a) Pd-containing precursor compound and Au-containing precursor compound;
 (b) Pt-containing precursor compound and Au-containing precursor compound;
 (c) Pd-containing precursor compound and Ag-containing precursor compound;
 (d) Pt-containing precursor compound and Ag-containing precursor compound;
 (e) Ag-containing precursor compound and Au-containing precursor compound; or
 (f) Pd-containing precursor compound and Pt-containing precursor compound.

If the named pairs of precursor compounds are applied to the support body successively, the first named precursor compound is also applied first. In principle, it is also conceivable that the same precursor compound is applied to the support body several times, and the support body is subjected to a temperature treatment between each of these several application steps.

If the further (or second) precursor compound is applied after the (first) temperature treatment, the support body with the applied further precursor compound is preferably subjected to a further (second) temperature treatment in the range of from 80° C. to 500° C. in a non-oxidizing atmosphere. For this further temperature treatment, the same conditions and preferred ranges apply as for the first temperature treatment.

The steps of applying the Pd-, Pt-, Ag- and/or Au-containing precursor compounds to the support body are preferably carried out until the Pd or Pt content after the temperature treatment is preferably in the range of from 0.0001 to 7 wt.-%, preferably 0.0002 to 5 wt.-%, and the Ag or Au content after the temperature treatment is preferably in the range of from 0.0003 to 4 wt.-%, preferably 0.0005 to 3 wt.-%, in each case relative to the total weight of the shell catalyst. If the shell catalyst is to be used for example as catalyst for the synthesis of vinyl acetate, its Pd or Pt content preferably lies in the range of from 0.3 to 2 wt.-%, more preferably in the range of from 0.4 to 1.8 wt.-% and most preferably in the range of from 0.5 to 1.6 wt.-%, and its Au content preferably lies in the range of from 0.1 to 0.9 wt.-% and more preferably 0.2 to 0.8 wt.-%. If the shell catalyst is to be used for example as catalyst for the selective hydrogenation of acetylene, its Pd or Pt content preferably lies in the range of from 100 to 300 ppm and more preferably in the range of from 150 to 250 ppm, and its Ag content preferably lies in the range of from 400 to 600 ppm and more preferably 450 to 550 ppm. If the shell catalyst is to be used for example as catalyst for the oxidation of alcoholic hydrocarbon compounds to aldehydes, ketones or carboxylic acids, its Pd or Pt content preferably lies in the range of from 3 to 7 wt.-% and more preferably in the range of from 4 to 6 wt.-%, and its Ag or Au content preferably lies in the range of from 1 to 5 wt.-% and more preferably 2 to 4 wt.-%. The duration of the application is thus chosen accordingly and can vary depending on the type, material and shape of the support body.

The application of the precursor compounds to the support body can be achieved using methods known per se. The precursor compounds are particularly preferably applied to the support body from one solution. Thus, the application of a solution containing the precursor compounds can take place by steeping, by immersing the support body in the precursor compound solutions or steeping it according to the incipient wetness method. However, it is difficult to produce a shell catalyst with a defined shell and a homogeneous metal distribution using these steeping methods.

The application step(s) in the method according to aspects of the invention is/are therefore preferably carried out by spraying the support body with a solution containing the precursor compound, wherein the support body is agitated in a process gas, e.g. in a coating drum, a fluid bed, a fluidized bed or in a static coating chamber of an Innojet AirCoater, into which hot air is blown, with the result that the solvent quickly evaporates. In this way, the precursor compounds are present in the named defined shell of the support body. The spraying rate is preferably chosen during the spraying such that a balance is achieved between the evaporation rate of the solvent and the feed rate of the precursor compounds on the support body. This makes it possible to set the desired shell thickness and palladium/platinum/gold/silver distribution in the shell. Depending on the spraying rate, the shell thickness can thus be continuously set and optimized, for example up to a thickness of 2 mm. But very thin shells with a thickness of less than 1000 µm are thus also possible.

If a fluid bed unit is used, it is preferred if the support bodies circulate elliptically or toroidally in the fluid bed. To give an idea of how the support bodies move in such fluid beds, it may be stated that in the case of "elliptical circulation" the support bodies move in the fluid bed in a vertical plane on an elliptical path, the size of the main and secondary axes changing. In the case of "toroidal" circulation the support bodies move in the fluid bed in a vertical plane on an elliptical path, the size of the main and secondary axes changing, and in a horizontal plane on a circular path, the size of the radius changing. On average, the support bodies move in a vertical plane on an elliptical path in the case of an "elliptical circulation", on a toroidal path in the case of a "toroidal circulation", i.e. a support body travels over the surface of a torus helically with a vertically elliptical section.

The application step(s) of the precursor compounds in the method according to aspects of the invention is/are preferably carried out by means of a fluid bed in a fluid bed unit. It is particularly preferred that the unit contains a so-called controlled air-glide layer. For one thing, the support bodies are thoroughly mixed by the controlled air-glide layer, wherein they simultaneously rotate about their own axis, and are dried evenly by the process air. For another, due to the consistent orbital movement, effected by the controlled air-glide layer, of the support bodies the support bodies pass through the spray procedure (application of the precursor compounds) at a virtually constant frequency. A largely uniform shell thickness, or penetration depth of the noble metals into the support body, of a treated phase of support bodies is thereby achieved. A further result is that the noble-metal concentration varies only relatively slightly over a relatively large area of the shell thickness, i.e. the noble-metal concentration describes an approximately rectangular function over a large area of the shell thickness, whereby a largely uniform activity of the resulting catalyst is guaranteed over the thickness of the noble metal shell.

Suitable conventional coating drums, fluidized bed units or fluid bed units for carrying out the application of the precursor compounds in the method according to aspects of the invention are known in the state of the art and are marketed for example by companies such as Heinrich Brucks GmbH (Alfeld, Germany), ERWEKA GmbH (Heusenstamm, Germany), Stechel (Germany), DRIAM Anlagenbau GmbH (Eriskirch, Germany), Glatt GmbH (Binzen, Germany), G. S. Divisione Verniciatura (Osteria, Italy), HOFER-Pharma Maschinen GmbH (Weil am Rhein, Germany), L.B. Bohle Maschinen and Verfahren GmbH (Enningerloh, Germany), Lödige Maschinenbau GmbH (Paderborn, Germany), Manesty (Merseyside, Great Britain), Vector Corporation (Marion (IA) USA), Aeromatic-Fielder AG (Bubendorf, Switzerland), GEA Process Engineering (Hampshire, Great Britain), Fluid Air Inc. (Aurora, Ill., USA), Heinen Systems GmbH (Varel, Germany), Hüttlin GmbH (Steinen, Germany), Umang Pharmatech Pvt. Ltd. (Maharashtra, India) and Innojet Technologies (Lörrach, Germany). Particularly preferred fluid bed equipment is sold with the name Innojet® AirCoater or Innojet® Ventilus by Innojet Technologies.

According to a further preferred embodiment of the method according to aspects of the invention, the support body is heated, for example by means of heated process air, during the application of the solution containing the precursor compound. The process air here preferably has a temperature of from 10 to 110° C., more preferably 40 to 100° C. and most preferably 50 to 90° C. The named upper limits should be adhered to in order to guarantee that the named outer shell has a small layer thickness with a high concentration of noble metal.

Air is preferably used as process air, but inert gases can also be used, such as for example nitrogen, $CO_2$, helium, neon, argon or mixtures thereof.

As already mentioned further above, the application of the precursor compound is preferably carried out by application from one solution. Pure solvents and solvent mixtures in which the selected metal compound is soluble and which, after application to the catalyst support, can be easily removed again from same by means of drying are suitable as solvents for the transition metal precursor compounds. Preferred solvents are unsubstituted carboxylic acids, in particular acetic acid, ketones, such as acetone, and in particular water. It is particularly preferred that the step(s) of application of the precursor compounds contains/contain a drying step, after the application, below the decomposition temperature of the precursor compounds, in particular at the temperatures named further above. By a decomposition temperature is meant the temperature at which the precursor compounds start to decompose.

The Pd- or Pt-containing precursor compound and/or the Ag- or Au-containing precursor compound is preferably a water-soluble compound.

The Pd- or Pt-containing precursor compounds are preferably selected from: nitrate compounds, acetate compounds, tetraammine compounds, diammine compounds, hydrogen carbonate compounds and hydroxidic metallate compounds.

Examples of preferred Pd-containing precursor compounds are water-soluble Pd salts. According to a particularly preferred embodiment of the method according to the invention, the Pd precursor compound is selected from the group consisting of $Pd(NH_3)_4(HCO_3)_2$, $Pd(NH_3)_4(HPO_4)$, ammonium Pd oxalate, Pd oxalate, $K_2Pd(oxalate)_2$, Pd(II) trifluoroacetate, $Pd(NH_3)_4(OH)_2$, $Pd(NO_3)_2$, $H_2Pd(OAc)_2(OH)_2$, $Pd(NH_3)_2(NO_2)_2$, $Pd(NH_3)_4(NO_3)_2$, $H_2Pd(NO_2)_4$, Na$_2$Pd(NO$_2$)$_4$, Pd(OAc)$_2$ as well as freshly precipitated Pd(OH)$_2$. The production of freshly precipitated Pd(OH)$_2$ is preferably carried out as follows: a 0.1 to 40 wt.-% aqueous solution is preferably produced from tetrachloropalladate. A base, preferably an aqueous solution of potassium hydroxide, is then added to this solution, until a brown solid, namely Pd(OH)$_2$ precipitates. To produce a solution for application to the catalyst support, the freshly precipitated Pd(OH)$_2$ is isolated, washed and dissolved in an aqueous alkaline solution. Dissolution preferably takes place at a temperature in the range of from 4 to 40° C., particularly preferably 15 to 25° C. A lower temperature is not possible because of the freezing point of water, a higher temperature brings with it the disadvantage that after a certain time Pd(OH)$_2$ precipitates again in the aqueous solution and does not dissolve.

Examples of preferred Pt-containing precursor compounds are water-soluble Pt salts. According to a particularly preferred embodiment of the method according to aspects of the invention, the Pt precursor compound is selected from the group consisting of Pt(NH$_3$)$_4$(OH)$_2$, Pt(NO$_3$)$_2$, K$_2$Pt(OAc)$_2$, (OH)$_2$, Pt(NH$_3$)$_2$(NO$_2$)$_2$, H$_2$Pt(OH)$_6$, Na$_2$Pt(OH)$_6$, K$_2$Pt(OH)$_6$, K$_2$Pt(NO$_2$)$_4$, Na$_2$Pt(NO$_2$)$_4$, Pt(OAc)$_2$, Pt(NH$_3$)$_4$(HCO$_3$)$_2$, Pt(NH$_3$)$_4$(HPO$_4$), Pt(NH$_3$)$_4$(NO$_3$)$_2$ as well as carboxylates of platinum, preferably the salts of aliphatic monocarboxylic acids with 3 to 5 carbon atoms, for example propionate or butyrate salt. Instead of NH$_3$ it is also possible to use the corresponding complex salts with ethylenediamine or ethanolamine as ligand.

According to a further preferred embodiment of the method according to aspects of the invention, the Pd or Pt nitrite precursor compounds can also be preferred. Preferred Pd or Pt nitrite precursor compounds are for example those which are obtained by dissolving Pd(OAc)$_2$ or Pt(OAc)$_2$ in an NaNO$_2$ or KNO$_2$ solution.

The Ag- or Au-containing precursor compounds are preferably selected from: acetate compounds, nitrite compounds and hydroxidic metallate compounds.

Examples of preferred Au-containing precursor compounds are water-soluble Au salts. According to a particularly preferred embodiment of the method according to aspects of the invention, the Au precursor compound is selected from the group consisting of KAuO$_2$, NaAuO$_2$, LiAuO2, RbAuO2, CsAuO2, NaAu(OAc)$_3$(OH), KAu(OAc)$_3$(OH), LiAu(OAc)$_3$(OH), RbAu(OAc)$_3$(OH), CsAu(OAc)$_3$(OH), KAu(NO$_2$)$_4$, HAu(NO$_3$)$_4$ and Au(OAc)$_3$. It may be advisable to add the Au(OAc)$_3$ or the KAuO$_2$ in each case freshly by precipitating the hydroxide from an auric acid solution, washing and isolating the precipitate as well as taking up same in acetic acid or KOH respectively. Potassium aurate in dissolved form is also particularly preferably used for application to the support body. The production of a potassium aurate solution is known in the literature and can be produced in accordance with the production methods disclosed in the documents WO 99/62632 and U.S. Pat. No. 6,015,769.

Examples of preferred Ag precursor compounds are water-soluble Ag salts. According to a particularly preferred embodiment of the method according to aspects of the invention, the Ag precursor compound is selected from the group consisting of Ag(NH$_3$)$_2$(OH), Ag(NO$_3$), K$_2$Ag(OAc)(OH)$_2$, Ag(NH$_3$)$_2$(NO$_2$), Ag(NO$_2$), Ag lactate, Ag trifluoroacetate, Ag salicylate, K$_2$Ag(NO$_2$)$_3$, Na$_2$Ag(NO$_2$)$_3$, Ag(OAc), ammoniac Ag$_2$CO$_3$ solution and ammoniac Ago solution. In addition to Ag(OAc) other carboxylates of silver can also be used, preferably the salts of the aliphatic monocarboxylic acids with 3 to 5 carbon atoms, for example propionate or butyrate salt.

According to a further preferred embodiment of the method according to aspects of the invention, Ag nitrite precursor compounds can also be preferred. Preferred Ag nitrite precursor compounds are for example those which are obtained by dissolving Ag(OAc) in an NaNO$_2$ or KNO$_2$ solution.

The named precursor compounds are cited only by way of example and any other precursor compounds which are substantially chloride-free can be used.

A solution for application of the precursor compounds to the support body of the method according to aspects of the invention preferably contains both a Pd or Pt precursor compound and an Ag or Au precursor compound. Thus, for example, separate solutions can be produced by first producing a Pd- or Pt-containing precursor compound solution and producing a further Ag- or Au-containing precursor compound solution. These two solutions can then be combined into one solution. In the solution of precursor compounds that contains both metal components, the Pd- or Pt-containing precursor compound is preferably present in a range of from 0.1 to 5 wt.-% and the Au- or Ag-containing precursor compound preferably in a range of from 0.05 to 3 wt.-%. For the selective hydrogenation of acetylene, the typical loadings lie in the range of 50 ppm to 1000 ppm Pd, preferably 100 ppm to 500 ppm Pd, and in the range of from 100 ppm to 2000 ppm Ag or Au, preferably 200 ppm to 1000 ppm Ag or Au.

After the application of the solution, the precursor compounds are preferably deposited on the support body by drying the solvent. The drying preferably takes place either by the process air in the fluid bed or the fluidized bed, by standing in air or in a drying oven, preferably at a temperature in the range of from 60° C. to 120° C.

The step of subjecting the support body containing the precursor compounds to a temperature treatment in the range of from 80° C. to 500° C. of the method according to aspects of the invention is preferably carried out immediately after the application and depositing of a Pd- or Pt-containing precursor compound and/or an Ag- or Au-containing precursor compound onto a support body. Thus, the precursor compounds are preferably not altered over the drying step between the steps of application and temperature treatment. It is particularly preferred that, between these steps, no intermediate calcining is carried out to the point of decomposition of the precursor compounds on the support body, however often these steps are repeated. The precursor compounds on the support body are thus subjected to the temperature treatment of the method according to aspects of the invention as they have been applied.

The temperature treatment preferably takes place in the range of more than or equal to 80 to 500° C., preferably in a range of from 90 to 450° C., particularly preferably in a range of from 100 to 400° C. and particularly preferably at a temperature in the range of from 100 to 350° C. A temperature above 80° C. is needed to decompose the precursor compounds sufficiently, in order that the metal components can be completely reduced. If a Pd- and Au-containing catalyst is produced in this way, the temperature treatment is preferably carried out in the range of from 100 to 200° C., more preferably in the range of from 120 to 190° C., even more preferably in the range of from 130 to 180° C., even more in the range of from 140 to 170° C. and most preferably in the range of from 150 to 160° C.

By a non-oxidizing atmosphere is meant in the present invention an atmosphere which contains no, or almost no, oxygen or other gases with an oxidizing action. The non-oxidizing atmosphere can be an inert gas atmosphere or a reducing atmosphere or a mixture of both gas variants.

In a variant of the method according to aspects of the invention, the reduction is carried out in an inert gas atmosphere. In this case, the counterions of the metal ion in the metal-containing precursor compound have a reductive action.

In a further variant of the method according to aspects of the invention, the temperature treatment can be carried out directly in a reducing atmosphere. In this case, the precursor compounds are decomposed at the same temperature of the temperature treatment and the metal component is reduced to the elemental metals. In other words, decomposition and reduction are carried out simultaneously at the same temperature in the reducing atmosphere. In this case, the temperature treatment preferably takes place in a range of more than or equal to 80° C. to 400° C., more preferably 80° C. to 300° C., even more preferably 100° C. to 250° C. and most preferably in the range of from 120° C. to 180° C.

In yet another variant of the method according to aspects of the invention, the temperature treatment is preferably carried out such that there is a change from an inert gas atmosphere to a reducing atmosphere during the temperature treatment. The precursor compounds are first decomposed at their decomposition temperature in an inert gas atmosphere and then the metal components are reduced to the elemental metals by the change to a reducing atmosphere. The temperature during the decomposition under inert gas preferably lies in the range of from 200 to 500° C., more preferably 250 to 450° C. and most preferably above 300° C. The temperature during the subsequent reduction then preferably lies in the range of more than or equal to 80° C. to 400° C., more preferably 80° C. to 300° C., even more preferably 100° C. to 250° C. and most preferably in the range of from 120° C. to 180° C.

All three method variants have the advantage that they can be carried out in one unit and surprisingly a precalcining or intermediate calcining in a further upstream or intermediate step in another unit can be dispensed with. Thus, the method according to aspects of the invention is carried out by dispensing with laborious cooling to below the decomposition temperature and heating to above the decomposition temperature. This method thus saves energy and costs. This was possible in particular because the starting materials were chloride-free starting compounds, which do not have such high decomposition temperatures as corresponding chlorine-containing compounds.

According to aspects of the invention, it is particularly preferred that the change from an inert gas atmosphere to a reducing atmosphere is carried out such that the temperature during the change does not fall below the temperature desired for the reduction.

$N_2$, He, Ne, Ar or mixtures thereof for example are used as inert gas. $N_2$ is particularly preferably used.

The component with reductive action in the reducing atmosphere is as a rule to be selected depending on the nature of the metal component to be reduced, but preferably selected from the group of gases or vaporizable liquids consisting of ethylene, hydrogen, CO, $NH_3$, formaldehyde, methanol, formic acid and hydrocarbons, or is a mixture of two or more of the above-named gases/liquids. The reducing atmosphere particularly preferably comprises hydrogen as reducing component. It is preferred in particular if the reducing atmosphere is formed by forming gas, a mixture of $N_2$ and $H_2$. The hydrogen content is in the range of from 1 vol.-% to 15 vol.-%. The method according to aspects of the invention is carried out for example with hydrogen (5 vol.-%) in nitrogen as process gas at a temperature in the range of from 80° C. to 500° C. over a period of for example from 1 to 5 hours.

The change named in the second method alternative from inert gas to a reducing atmosphere preferably takes place by feeding one of the named reducing components into an inert gas atmosphere. Hydrogen gas is preferably fed in. The feeding of a gas with a reductive action to the inert gas has the advantage that the temperature does not fall substantially, or not down to or below the lower limit of 80° C. desired for the reduction, with the result that there is no need for another cost- and energy-intensive heating necessitated by a corresponding total atmosphere exchange.

In a particularly preferred embodiment, the support body containing the precursor compounds is not exposed to a temperature greater than or equal to 300° C. in an oxidizing atmosphere before the temperature treatment. In this way, it is guaranteed that the support body with the precursor compounds applied to it is subjected to the temperature treatment, just like the precursor compounds are. In other words: a cost-intensive precalcining of the impregnated support body to the metal oxides can be dispensed with.

A further embodiment relates to the use of a shell catalyst produced using a method according to aspects of the invention for the production of vinyl acetate monomer (VAM), or in the reduction or oxidation of hydrocarbon compounds, in particular the oxidation of alcohols to aldehydes, ketones or carboxylic acids.

The catalyst according to aspects of the invention is preferably used for the production of VAM. Generally this takes place by passing acetic acid, ethylene and oxygen or oxygen-containing gases over the catalyst according to the invention at temperatures of 100-200° C., preferably 120-200° C., and at pressures of 1-25 bar, preferably 1-20 bar, wherein non-reacted educts can be recycled. Expediently, the oxygen concentration is kept below 10 vol.-%. Under certain circumstances, however, a dilution with inert gases such as nitrogen or carbon dioxide is also advantageous. Carbon dioxide is particularly suitable for dilution as it is formed in small quantities in the course of VAM synthesis. The formed vinyl acetate is isolated with the help of suitable methods, which are described for example in U.S. Pat. No. 5,066,365 A.

EXAMPLES

Comparison Example 1

Shell Catalyst A

A shell catalyst A was produced in the following way: 1.2 litres of a silica support in spherical shape with a diameter of 5 mm, a density of 540 g/L, a pore volume of 0.68 ml/g and a pH of 4.0 in a 10 wt.-% suspension, was impregnated with 440 ml of an aqueous solution of $Na_2PdCl_4$ and $HAuCl_4$ containing 3.96 g Pd and 1.8 g Au (99.8 of the absorption capacity of the support). A vessel containing this mixture was rotated mechanically until the solution was completely absorbed by the silica support. 500 ml of a solution containing 25.2 g $Na_2SiO_3.9H_2O$ was then added to the support, with the result that this was completely covered. This was left to stand for 12 hours at room temperature. After this time, the liquid surrounding the support had a pH of 7.7. 25 ml of an 85% hydrazine hydrate solution was then added, lightly mixed and the resulting mixture was left to stand for 4 hours at room temperature in order to reduce the palladium and gold. The catalyst was then washed three times with distilled water by decanting, followed by continuous washing over 16 hours at a washing rate of 1-2 litres distilled water per hour. After this period, the washing water was free of chlorides, which was proved by the absence of a precipitate when silver nitrate was added.

The catalyst was then dried for 4 hours at 110° C., impregnated with a solution containing 36 g potassium acetate (corresponds to 30 g potassium acetate per litre catalyst) and dried again. The thus-obtained catalyst contained 3.32 g/l palladium and 1.39 g/l gold, compared with 3.3 g/l palladium and 1.5 g/l gold in the starting compounds. Thus, 100% palladium and 92.7% gold were precipitated.

Comparison Example 2

Shell Catalyst B

The production of a shell catalyst B took place according to the following procedure: coating of 53.21 g of a 3.12% $Pd(NH_3)_4(OH)_2$ solution onto 100 g KA-160 support spheres (manufacturer: Süd-Chemie AG) (standard conditions: 70° C. coating temperature, 2×1 tube, 80% spraying rate in the Innojet AirCoater 025), followed by intermediate calcining at 350° C. for 4 h in air, then coating-on of 14.66 g of a 7.54% $KAuO_2$ solution, then drying in the fluidized bed at 90° C. for 45 min, then reduction with forming gas in the gas phase at 150° C. for 5 h, then IW (incipient wetness) impregnation with aqueous KOAc solution, and finally drying at 90° C. in the fluidized bed for 45 min.

Comparison Example 3

Shell Catalyst C

The production of a shell catalyst C took place according to the following procedure: a catalyst precursor was produced analogously to Example 1, with the difference that reduction was in the gas phase with forming gas at 200° C. for 5 h and impregnation with KOAc had not yet taken place. This catalyst precursor was further processed as follows: coating-on of 8.61 g of a 7.54% $KAuO_2$ solution, followed by reduction in the gas phase with forming gas at 150° C. for 5 h, then impregnation with KOAc by the incipient wetness method.

Comparison Example 4

Shell Catalyst D

The production of a shell catalyst D took place according to the following procedure: coating of 35.20 g of a 3.12% $Pd(NH_3)_4(OH)_2$ solution onto 100 g KA-160 support spheres, followed by drying in the fluidized bed at 90° C. for 45 min, then intermediate calcining at 350° C. for 4 h in air, then coating-on of 11.64 g of a 7.54% $KAuO_2$ solution (not the standard conditions in the coater, but 60° C. coating temperature, 3×1 tube, 100% spraying rate), then drying in the fluidized bed at 90° C. for 45 min, then reduction with forming gas in the gas phase at 150° C. for 5 h, then IW (incipient wetness) impregnation with aqueous KOAc solution, and finally drying at 90° C. in the fluidized bed for 45 min.

Example 1 (According to the Invention)

Shell Catalyst E

A mixed solution of 24.85 ml of a 4.4% $Pd(NH_3)_4(OH)_2$ solution in 150 ml $H_2O$ and 5.74 ml of a 9.9% $KAuO_2$ solution in 150 ml $H_2O$ is coated at 70° C. onto 100 g KA-160 supports (5 mm), followed by drying at 90° C. for 45 min in the fluidized bed and then reduction without intermediate calcining at 350° C. for 4 h with forming gas. IW (incipient wetness) impregnation with aqueous KOAc solution follows (16.79 g 2 molar KOAc was weighed in and topped up with water to 98% of the water absorption of the support for the incipient wetness impregnation (pore-filling method)) for 1 h in a rotating round-bottomed flask (Rotavapor) and the final drying in the fluidized bed at 90° C. for 45 min. The metal contents determined by chemical analysis (LOI-free) (LOI=loss on ignition) of the finished catalyst are 1.02% Pd and 0.57% Au.

Example 2

Results

Figure 1:
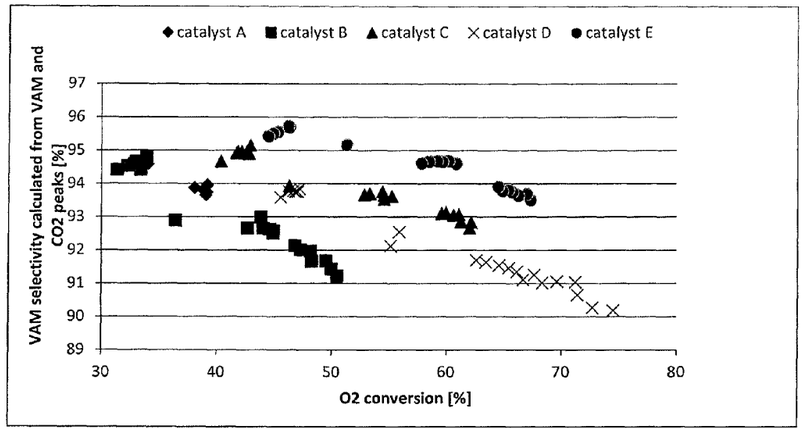
FIG. 1 shows a diagram in which the vinyl acetate monomer selectivity of the tested catalysts is plotted on the Y-axis. The oxygen conversion of six tested catalysts is shown on the X-axis.

The results for the shell catalysts A to E as regards the selectivity for the synthesis of vinyl acetate as a function of the oxygen conversion are shown in FIG. 1 and Tables 1 and 2. For this, acetic acid, ethylene and oxygen were each passed over the catalysts A to E at a temperature of 140° C./12 h—>144° C./12 h—>148° C./12 h (these are the respective reaction temperatures that apply in turn during the automated execution of the screening protocol, i.e. measurement is carried out for 12 h at 140° C., then for 12 h at 144° C., and then for 12 h at 148° C. reactor temperature) and a pressure of 7 bar. The concentrations of the components used were: 39% ethylene, 6% $O_2$, 0.6% $CO_2$, 9% methane, 12.5% acetic acid, remainder $N_2$.

The formed vinyl acetate is isolated with the help of suitable methods, which are described for example in U.S. Pat. No. 5,066,365 A.

TABLE 1

| Catalyst A | | Catalyst B | | Catalyst C | |
|---|---|---|---|---|---|
| VAM selectivity from VAM and $CO_2$ peaks [%] | $O_2$ conversion [%] | VAM selectivity from VAM and $CO_2$ peaks [%] | $O_2$ conversion [%] | VAM selectivity from VAM and $CO_2$ peaks [%] | $O_2$ conversion [%] |
| 94.5403736 | 33.38043263 | 92.8868103 | 36.41085397 | 93.93080782 | 46.2697302 |
| 94.54486515 | 33.73055667 | 92.50913818 | 44.86784605 | 93.62038499 | 55.25321859 |
| 94.58527534 | 34.01582915 | 92.57239016 | 44.88278355 | 93.52413305 | 54.57788196 |
| 94.43825207 | 33.10042502 | 92.62715235 | 44.5457634 | 93.64021575 | 54.58827647 |
| 93.64638431 | 39.03542836 | 92.65624986 | 43.99216432 | 93.7488175 | 54.43298037 |
| 93.73965914 | 39.12083312 | 92.97857691 | 43.81941636 | 93.69595227 | 53.33102061 |
| 93.77144861 | 39.02310831 | 92.65806345 | 42.62705498 | 93.66026672 | 52.87150042 |
| 93.78511742 | 38.83466548 | 91.22106445 | 50.47282872 | 92.65953438 | 62.01286258 |
| 93.95832411 | 39.18493382 | 91.43004144 | 49.99063328 | 92.83067608 | 62.16211753 |
| 93.86783871 | 38.08404005 | 91.67029341 | 49.50882991 | 92.85039609 | 61.26118317 |
| | | 91.66434729 | 48.24962899 | 93.06248463 | 61.09097702 |
| | | 91.96231232 | 48.16275199 | 93.04816286 | 60.63690859 |
| | | 92.00149982 | 47.28660329 | 93.12556275 | 59.99297675 |
| | | 92.12220312 | 46.79208048 | 93.0977835 | 59.6039523 |
| | | 94.40299741 | 33.38791913 | 94.90113926 | 42.7573582 |
| | | 94.78763983 | 33.93667492 | 95.15124024 | 42.84849106 |
| | | 94.59378223 | 32.85605593 | 94.96082578 | 42.12923203 |
| | | 94.65897141 | 32.98446753 | 94.96251057 | 41.82625695 |
| | | 94.52912807 | 32.25492922 | 94.91608119 | 41.68556177 |
| | | 94.41133174 | 31.36055782 | 94.67162429 | 40.35968328 |

TABLE 2

| Catalyst D | | Catalyst E | |
|---|---|---|---|
| VAM selectivity from VAM and $CO_2$ peaks [%] | $O_2$ conversion [%] | VAM selectivity from VAM and $CO_2$ peaks [%] | $O_2$ conversion [%] |
| 92.11570687 | 55.16832068 | 95.16626159 | 51.31941346 |
| 92.54403671 | 55.91630926 | 94.60282084 | 60.82778578 |
| 91.10913177 | 66.69895594 | 99.00530146 | 54.54899079 |
| 91.34254639 | 66.13532853 | 94.6888208 | 60.19573635 |
| 91.45795194 | 65.43206064 | 94.65323656 | 59.67685586 |
| 91.53140581 | 64.5682873 | 94.67307711 | 59.19945111 |
| 91.63454785 | 63.44787341 | 94.65994408 | 58.49052619 |
| 91.68581884 | 62.60491008 | 94.61219729 | 57.83089447 |
| 90.17785905 | 74.48615129 | 93.4965516 | 67.35493262 |
| 90.26509075 | 72.71082346 | 93.6796574 | 67.02249992 |
| 90.65168707 | 71.39541951 | 93.63903973 | 66.2732481 |
| 91.04027027 | 71.22225341 | 93.73955499 | 65.76120076 |
| 91.05312322 | 69.65454687 | 93.8135574 | 65.41911089 |
| 91.01377644 | 68.36620065 | 93.77271043 | 64.87770278 |
| 91.25005352 | 67.67890203 | 93.89777215 | 64.50846478 |
| 93.74920706 | 47.00811439 | 95.68704404 | 46.30596571 |
| 93.84416715 | 47.16545977 | 95.69710367 | 46.18271114 |
| 93.75034726 | 46.80400553 | 95.72296786 | 46.2103981 |
| 93.78314876 | 46.64050042 | 95.54650433 | 45.25139087 |
| 93.76522414 | 46.21345306 | 95.50444649 | 44.86478531 |
| 93.58149034 | 45.51768132 | 95.41938261 | 44.42558348 |

Example 3 (According to the Invention)

Shell Catalyst F 0.77 g of a 3.12% $Pd(NH_3)_4(OH)_2$ solution (diluted with 100 ml water) was coated onto 120 g CTR 4*4 mm support tablets ($Al_2O_3$, BET 3.8 $m_2/g$) (standard conditions: 70° C. coating temperature, 2×1 tube, 80% spraying rate in the Innojet AirCoater 025), followed by coating-on of 0.40 g of a 7.54% $KAuO_2$ solution (diluted with 100 ml water) without prior calcining, then drying in the fluidized bed at 90° C. for 45 min, then reduction with forming gas in the gas phase at 150° C. for 3 h.

Example 4 (According to the Invention)

Shell Catalyst G 0.77 g of a 3.12% $Pd(NH_3)_4(OH)_2$ solution (diluted with 100 ml water) was coated onto 120 g CTR 4*4 mm support tablets ($Al_2O_3$, BET 3.8 $m_2/g$) (standard conditions: 70° C. coating temperature, 2×1 tube, 80% spraying rate in the Innojet AirCoater 025), followed by coating-on of 5.08 g of a 1.30% Ag(OAc) solution (diluted with 100 ml water) without prior calcining, then drying in the fluidized bed at 90° C. for 45 min, then reduction with forming gas in the gas phase at 150° C. for 3 h.

Example 5 (According to the Invention)

Shell Catalyst H 0.77 g of a 3.12% $Pd(NH_3)_4(OH)_2$ solution (diluted with 100 ml water) was coated onto 120 g CTR 4*4 mm support tablets ($Al_2O_3$, BET 3.8 $m_2/g$) (standard conditions: 70° C. coating temperature, 2×1 tube, 80% spraying rate in the Innojet AirCoater 025), followed by coating-on of 0.36 g of a 10.0% $Ag(NO_3)$ solution (diluted with 100 ml water), then coating-on of 0.08 g of a 7.54% $KAuO_2$ solution, then drying in the fluidized bed at 90° C. for 45 min, then reduction with forming gas in the gas phase at 150° C. for 3 h.

Example 6 (According to the Invention)

Shell Catalyst I

A catalyst was produced analogously to Example 3, with the difference that the reduction was in the gas phase with forming gas at 100° C. for 3 h.

Example 7 (According to the Invention)

Shell Catalyst J

A catalyst was produced analogously to Example 3, with the difference that the two noble metal solutions were combined and were coated on simultaneously under standard conditions (70° C. coating temperature, 2×1 tube, 80% spraying rate in the Innojet AirCoater 025), followed by drying in the fluidized bed at 90° C. for 45 min, then reduction with forming gas in the gas phase at 150° C. for 3 h.

Comparison Example 5

Shell Catalyst K

A catalyst was produced analogously to Example 3, with the difference that, before the application of the gold compound, an intermediate calcining was carried out for 3 h at 375° C.

Comparison Example 6

Shell Catalyst L

A catalyst was produced analogously to Example 4, with the difference that, before the application of the silver compound, an intermediate calcining was carried out for 3 h at 350° C.

Comparison Example 7

Shell Catalyst M

A catalyst was produced analogously to Example 3, with the difference that, before the treatment with forming gas, calcining was carried out for 3 h at 375° C.

Example 8

Results

The activity, stability and selectivity of the catalysts F-M were tested in the selective hydrogenation of acetylene. For this, a mixture of ethylene and acetylene was produced based on the conditions of a "front-end" hydrogenation of a deethanizer unit of an ethylene plant (GHSV 7000, pressure 500 psig). The tests were carried out analogously to the usual technical conditions: Approximately 25 ml of the catalyst formulation is loaded into a double-walled stainless steel reactor with an internal diameter of 1.25 cm, which is heated via a thermostatically controlled water bath. The lowest starting temperature at which less than 25 ppm acetylene is recorded at the outlet of the reactor is called T1. T1 is the measure of the activity of the catalyst.
Acetylene Conversion:

(ppm acetylene at inlet−ppm acetylene at outlet)/
(ppm acetylene at inlet)

If, after reaching this temperature, the reactor temperature is further increased, the hydrogenation of ethylene also results, in addition to the desired hydrogenation of acetylene. The selectivity thus decreases.
Acetylene Selectivity:

(ppm acetylene at inlet−ppm acetylene at outlet−ppm
ethane at outlet+ppm acetylene at outlet)/(ppm
acetylene at inlet)

If the temperature is further increased, the rate of reaction of the hydrogenation of acetylene and ethylene increases further. As the reaction is exothermic, reaction heat is also increasingly released. From a certain point, T2, a "runaway" reaction finally occurs and selectivity is completely lost. T2 is defined as the point at which a 4% loss of hydrogen occurs. The stability of a catalyst is defined as the difference between T1 and T2, the higher this is, the more stable the catalyst is. The temperature of the reaction is varied in the range of from 30 to 104° C. The results of the tests are summarized in Table 3.

TABLE 3

| Catalyst | T1 [° C.] | T2 [° C.] | ΔT [° C.] | Selectivity at T1 [%] |
| --- | --- | --- | --- | --- |
| F | 59 | 92 | 31 | 67 |
| G | 54 | 80 | 26 | 66 |
| H | 63 | 103 | 30 | 80 |
| I | 64 | 99 | 35 | 59 |
| J | 61 | 97 | 36 | 76 |
| K | 61 | 71 | 12 | 28 |
| L | 57 | 71 | 14 | 45 |
| M | 63 | 74 | 11 | 42 |

The catalysts F-J according to the invention show a larger temperature window as well as better selectivity than the catalysts K, L and M, for comparable activities (with a tendency to be slightly higher).

What is claimed:

1. A method for producing a shill catalyst, comprising the steps of
   mixing one or more support bodies by a controlled glide layer consisting of one of air and inert gas;
   during the mixing, spraying the one or more support bodies with a first solution comprising a substantially chloride-free Pd-, Pt-, Ag- or Au-containing first precursor compound, and
   subjecting the one or more support bodies to a first temperature treatment in the range of from 80° C to 500° C in a non-oxidizing atmosphere.

2. The method according to claim 1, wherein, before or after the first temperature treatment, the one or more support bodies are mixed by a controlled glide layer comprising at least one of air and inert gas, and, during the mixing, frayed with a second solution comprising a second substantially chloride-free Pd-, Pt-, Ag- or Au-containing precursor compound.

3. The method according to claim 2, wherein the first precursor compound and the second precursor compound form the following pairs:
   (a) Pd-containing precursor compound and Au-containing precursor compound;
   (b) Pt-containing precursor compound and Au-containing precursor compound;
   (c) Pd-containing precursor compound and Ag-containing precursor compound;
   (d) Pt-containing precursor compound and Ag-containing precursor compound;
   (e) Ag-containing precursor compound and Au-containing precursor compound; or
   (f) Pd-containing precursor compound and Pt-containing precursor compound.

4. The method according to claim 2, wherein the second precursor compound is applied after the temperature treatment, and the one or more support bodies with the applied second precursor compound is subjected to a second temperature treatment in the range of from 80° C. to 500° C. in a non-oxidizing atmosphere.

5. The method according to claim 4, wherein there is no intermediate calcining between the spraying of the one or more support bodies with the second solution and the second temperature treatment.

6. The method according to claim 2, wherein the first precursor compound is a Pd- or Pt-containing precursor compound, and the second precursor compound is an Au-containing precursor compound.

7. The method according to claim 6, wherein the Pd or Pt content lies in the range of from 0.3 to 2wt.-% relative to the total weight of the catalyst and the Au content lies in the range of from 0.1 to 0.9 wt.-% relative to the total weight of the catalyst.

8. The method according to claim 2, wherein the first precursor compound is a Pd- or Pt-containing precursor compound, and the second precursor compound is an Ag-containing precursor compound.

9. The method according to claim 8, wherein the Pd or Pt content lies in the range of from 100 to 300 ppm relative to all parts of the catalyst at and the Ag content lies in the range of from 400 to 600 ppm relative to all parts of the catalyst.

10. The method according to claim 2, wherein the first precursor compound is a Pd- or Pt-containing precursor compound and the second precursor compound is an Ag- or Au-containing precursor compound.

11. The method according to claim 10, wherein the Pd or Pt content lies in the range of from 3 to 7 wt.-% relative to the total weight of the catalyst and the Ag or Au content lies in the range of from 1 to 5 wt.-% relative to the total weight of the catalyst.

12. The method according to claim 1, wherein the Pd- and Pt-containing precursor compounds are independently selected from the group consisting of nitrate compounds, acetate compounds, tetraammine compounds, diamine compounds, hydrogen carbonate compounds and hydroxidic metallate compounds.

13. The method according to claim 1, wherein the Ag- and Au-containing precursor compounds are independently selected from the group consisting of acetate compounds, nitrite compounds and hydroxidic metallate compounds.

14. The method according to claim 1, wherein the non-oxidizing atmosphere of the first treatment and the second temperature treatment independently comprise an inert gas atmosphere or a reducing atmosphere.

15. The method according to claim 14, wherein the reducing atmosphere is formed by forming gas.

16. The method according to claim 14, wherein, during the first temperature or the second temperature treatment, a change from an inert gas atmosphere to a reducing atmosphere takes place.

17. The method according to claim 16, wherein the change from inert gas to a reducing atmosphere takes place by adding hydrogen gas to the inert gas.

18. The method according to claim 17, wherein the change from an inert gas atmosphere to a reducing atmosphere is carried out such that the temperature does not fall below 80° C during the change.

19. The method according to claim 1, wherein there is no intermediate calcining between the spraying of the one or more support bodies with the first solution and the first temperature treatment.

20. The method according to claim 1, wherein the one or more support bodies have a diameter, length or width in the range of from 1 to 10 mm.

* * * * *